United States Patent [19]

Falagiani et al.

[11] Patent Number: 5,354,848
[45] Date of Patent: Oct. 11, 1994

[54] CHEMICALLY MODIFIED ALLERGENS AND PROCESS FOR THE PREPARATION THEREOF

[75] Inventors: Paolo Falagiani, Milan; Oreste Brenna, Cologno Monzese; Giovanni Mistrello, Milan, all of Italy

[73] Assignee: Laboratorio Farmaceutico Lofarma S.r.l., Milan, Italy

[21] Appl. No.: 588,344

[22] Filed: Sep. 26, 1990

[30] Foreign Application Priority Data

Oct. 6, 1989 [IT] Italy ................. 48431 A/89

[51] Int. Cl.$^5$ ............. A61K 39/35; A61K 39/36; C07K 3/08
[52] U.S. Cl. ................. 530/395; 424/275.1; 530/370; 530/404; 530/405; 530/806
[58] Field of Search .......... 424/91, 88; 530/402, 530/403, 404, 405, 406, 370, 395, 806, 862; 514/8

[56] References Cited

U.S. PATENT DOCUMENTS

| | | | |
|---|---|---|---|
| 3,893,993 | 7/1975 | Mullan et al. | 530/405 |
| 4,222,907 | 9/1980 | Katz | 424/91 |
| 4,234,569 | 11/1980 | Marsh | 530/379 |
| 4,469,677 | 9/1984 | Michael et al. | 530/379 |
| 4,629,706 | 12/1986 | Hammand et al. | 424/91 |

FOREIGN PATENT DOCUMENTS 1282163  8/1973  United Kingdom .

OTHER PUBLICATIONS

Maasch et al., Clin. Rev. Allergy, vol. 5 pp. 89–106 (1987).
Steinbecher et al., J. Lipid Res., vol. 25 (10), pp. 1109–1116 (1984).
Yang et al., The Snake, vol. 14, pp. 110–118 (1982).
Yang et al., J. Chinese Biochem. Soc., vol. 7, No. 2, pp. 62–77 (1978).
Yang et al.; Toxicon, vol. 19 No. 5, pp. 645–659, (1981).
Veleva, Vet. Med. Nauki, 13(10), pp. 42–54 (1976).
King et al., Immunochem., vol. 11, pp. 87–92 (1974).
J. Allerg. Clin. Immunol., vol. 80, No. 5, issued Nov. 1987, Wadec et al., "Development of specific IgE antibodies . . . ", pp. 695–698.
Fudenberg et al., "Basic & Clinical Immunology", published 1776, Lange Medical Publications (Los Altos), pp. 208, 226.
Feeney et al., Carbonyl–Amine Reactions in Protein Chemistry, 1975, vol. 29, pp. 135–203 (Academic Press, N.Y.).
Patterson et al., Polymerized Ragweed Antigen E., May 1973, pp. 1413–1418.
Moran et al., Chemical Modification of Crude Timothy Grass Pollen Extract, Sep. 1, 1975, pp. 693–708.
Timasheff, Serge N., Methods in Enzymology Enzyme Structure, 1972, pp. 579–585.
Newell, John M., A Review of Chemical Studies on the Allergens in Pollens, pp. 176–203.
Habeeb, Determination of Free Amino Groups in Proteins by . . . Acid, Jul. 27, 1965, pp. 328–336.
Stark et al., The Use of Cyanate for the Determination of $NH_2$-terminal Residues in Protein, Jul. 27, 1962, pp. 214–226.
Ovary, Z., Cutaneous Anaphylaxis in the Albino Rat, pp. 293–301.
Yman, et al., Rast-Based Allergen Assay Methods, 1975, pp. 151–165.
Ouchterlony, Orjan, Diffusion–in–Gel Methods for Immunological Analysis, Jan., 1957, pp. 1–78.
Fearon, William R., Urease, Part I. The Chemical Changes Involved in the Zymolysis of Urea, Jan. 9, 1923, pp. 84–93.

Primary Examiner—Jeffrey E. Russel
Attorney, Agent, or Firm—Samuels, Gauthier & Stevens

[57] ABSTRACT

Chemically modified allergens, whose allergenic activity is reduced with respect to that of the corresponding native allergenic material, which are capable of inducing specific antibodies addressed towards said native allergenic material, wherein a portion of the primary amino groups of the protein molecule of the native allergen are chemically modified so as to give simple or substituted carbamylic amino groups, or substituted thiocarbamylic amino groups, or possibly substituted guanidino groups, and process for the production thereof. The allergens so modified are not polymerized with each other, they are soluble in water media, they are resistent to tryptic hydrolysis and they show particularly suitable for being administered in hyposensitizing therapeutic treatments.

5 Claims, No Drawings

CHEMICALLY MODIFIED ALLERGENS AND PROCESS FOR THE PREPARATION THEREOF

CROSS-REFERENCE TO RELATED APPLICATION

This application is based on Italian Application 48431-A89 filed Oct. 6, 1989.

BACKGROUND OF THE INVENTION

A. Field the Invention

This invention relates to chemically modified allergens and to the process for the preparation thereof. More particularly, this invention relates to a new type of chemically modified allergens, which are effective for treating allergic diseases, as well as to the method for the preparation thereof.

Description of the Related Art

It is already known that many people suffer from troubles of allergic type; the most common symptoms are asthma, hay fever and conjunctivitis, urticaria. The mechanism that causes such troubles is usually due to an allergic sensitization state consisting in the hyperproduction of antibodies of the IgE class which have an affinity for ubiquitous allergens, as for instance, pollens, house dust mites, fungi spores, and so on. The antibodies of the IgE class do not exert any protective role usually exerted by the antibodies of the other classes, but in addition they cause a complex cellular reaction when they react with allergens for which they have an affinity, as they have the capability of binding to tile membrane of the mast cells of the mucosa and to the basophilic leucocytes, said reaction resulting in the release of vasoactive amines (for instance histamine) and other compounds which are the actual mediators of the allergic reactions and are responsible for the same.

In order to reduce or to remove the allergic troubles, the specific hyposensitizing therapy has been practised for many decades. It consists in administering to the allergic patient, generally through the subcutaneous injection route, progressively increasing doses of those allergens to which the patient is sensitive, such allergens being identified during previous diagnostic investigation. The traditional allergenic extracts are made up of water solutions of allergens having a pH value close to neutrality (pH 7.0-7.4) and an osmotic strength similar to that of the serum.

The mechanisms through which said specific hyposensitizing therapeutic treatment results in the decrease or in the disappearance of the allergic symptoms are manifold; the most known and certainly the most important of them is the following: the repeated injection of the allergen induces in the organism the production of allergen-specific antibodies of the IgG class, called "blocking antibodies", capable of reacting with the allergen and of preventing the same from reacting with the IgEs so causing the pathogenic reaction previously outlined.

In order that said specific hyposensitizing therapeutical treatment could be efficient, it is necessary that the dose of the allergen which is injected in total is high.

Though it is universally accepted because of its effectiveness, said specific hyposensitizing therapeutic treatment shows however some drawbacks which are due to the unwanted reactions that can occur following the injection of the allergen. Indeed, local reactions can occur just at the injection site (large red patchs, reddening, itch, and so on), or systemic reactions (rhinitis or asthma, and anaphylactic shock).

In order to reduce such undesired reactions and hence to make the specific hyposensitizing therapy safer, allergenic extracts of a depot type, i.e. slow-absorption allergenic extracts, have been realized in the most recent years, in which extracts of the allergens are precipitated or adsorbed with aluminum hydroxide, tyrosine or calcium phosphate, in order to slow down the absorption in the organism and then to reduce the reactivity: with such type of extracts, patients can better tolerate the inoculation of the extract and with a less number of undesired reactions.

Though such depot type allergenic extracts represent an improvement, however they are not the optimal and definitive solution to the problem because a certain percentage of patients responds to them also with undesired reactions, both local and systemic. In an attempt to obviate such drawbacks, chemical modifications of the allergens have been tried, such as decreasing their allergenic reactivity substantially (i.e., the capability of reacting with the IgEs bonded to the tissue mast cells and then of causing the pathogenic reaction), while keeping their immunogenic power unchanged (i.e., the capability of inducing the formation of blocking antibodies of the IgG class). Some authors have employed the term "allergoids" to point out the allergens so modified.

A method proposed to produce modified allergens having in part the required features is the denaturation method with 8 M urea. Indeed, it has been shown that, by exposure of the antigen E of Ambrosia elatior pollen (a very important allergenic plant growing in the United States) to the dissociating action of an 8 M solution of urea, such antigen lost a large amount of its capability of reacting with the IgEs, though it kept the hyposensitizing capability after injection for therapeutical purposes. However, tests in human subjects, following to such quite encouraging experiments performed on mice, gave conflicting results. Moreover, the method disclosed above seems to be employable just for the antigen E of Ambrosia elatior, made up of two polypeptidic subunits put together by non-covalent bonds, which is particularly sensitive to the denaturing action of dissociating agents, such as 8 M urea.

Another method which is already known for obtaining the chemical modification of allergens, is the treatment with aldehydes, the most employed of them being formaldehyde or glutaraldehyde. The reactions between aldehyde functions and protein amino groups are described for instance by R. E. Feehey, G. Blankenhorn and H. B. F. Dixon, Adv. Prot. Chem. 29, 135-203, 1975; it is to be kept in mind that almost all allergens are chemically constituted of glycoprotein molecules, in which the protein component is the part relevant to give its features of immunologic specificity.

It has been shown that by treating with formaldehyde Lolium perenne's and Ambrosia's allergens, a 100-10,000 times decrease in the allergenic reactivity is obtained with respect to the native allergen. The conditions for the chemical modification are described by Marsh in "The Antigens" vol. III, pg. 317, Ed. Sela M., Academic Press, New York. The product so obtained keeps a satisfying immunogenic capability when injected for therapeutic purposes, but the reactivity changes from patient to patient in a wide degree: as a consequence, doses as well as dosage schemes which may be optimal for some patients, might happen to be not so for others.

The reaction with glutaraldehyde, as this is a bifunctional aldehyde, causes the formation of a mixture of polymers having various molecular weights (see for instance R. Patterson, J. Immunol. 110, 1413, 1973, in which the antigen E of Ambrosia is subjected to polymerization with glutaraldehyde, so obtaining a product having an allergenic activity reduced by 10-100 times, or otherwise see D. M. Moran and A. W. Wheeler, Int. Archs. Allergy and Applied Immunology, 50, 693, 1976, in which a similar procedure is applied to allergens of Phleum pratense). However, the polymerization method employing glutaraldehyde shows two drawbacks:

1) the removal of macromolecules from the organism, such as those which are obtained by means of that procedure (from $2 \times 10^5$ to $2 \times 10^7$ daltons) is difficult, so that toxicity is likely to be high;

2) the final addition of glycine, lysine or other amino acids or compounds containing at least one amino group for stopping the reaction results in products of synthesis between glycine and glutaraldehyde, which products have no relationship with the native allergen and are likely to bring about new allergenic determinants which are useless in regard to the therapeutic effects.

Another chemical procedure for modifying allergens is the object of the UK patent No. 1282163, in which the reaction process of Gramineae pollens allergens with an inorganic cyanate, or with a polyaldehyde or carbodiimide is described. The object of the process consists in the preparation of modified allergenic material, substantially insoluble or just partially soluble in water.

The alkaline cyanate procedure is carried out in an acid medium, in particular at a pH of 5. The occurring reaction is the condensation of the amino groups of the allergen with the carboxyl groups (activated by cyanic acid in the form of a mixed anhydride) of the allergen itself (Methods in Enzymology 25, 579, 1972). Any way, by means of the procedure disclosed in the UK patent No. 1,282,163, the allergenic material is polymerized till it becomes insoluble in water or in water solutions.

The procedures of the prior art described above result anyway in all cases in the formation of polymeric derivatives of the allergen, so that they are characterized by a lower bond valence with respect to the specific antibodies of the IgE class.

SUMMARY

The object of the present invention consists in providing a new type of chemically modified allergens having the capability of inducing specific antibodies of the IgG class towards the corresponding native allergens and also having a much reduced reactivity, as well as no one of the drawbacks which are characteristic of the so-called "allergoids" described previously.

To that end, we had the idea of modifying selectively some chemical groups present in the molecule of the native allergen, so as to modify the affinity for the IgEs fixed to the cellular receptors, without causing the polymerization of the allergens themselves. This has been obtained by subjecting the allergenic molecules to carbamylation (or thiocarbamylation, or to the formation of guanidine-type groups) of the primary amino groups of the protein part thereof, in particular, of the terminal amino group and of the epsilon-amino groups of lysine residues.

The carbamylation reaction of a protein molecule, which is already known per se to those who are skilled in the art, can also go on in other chemical groups which are present in the protein chain, such as the hydroxyl group of tyrosine, the sulfhydryl group of cysteine, the carboxyl group of aspartic and glutamic acids and the imidazole group of histidine (Methods in Enzymology, 25, 579, 1972). In the conditions of a physiological pH, all such derivatives are unstable, whereas the reaction products of carbamylation of the alpha- and the epsilon-amino groups are on the contrary very stable.

The carbamyl and thiocarbamyl derivatives of the allergens suggested according to the present invention, as well as the guanidine-type derivatives, have been shown to be capable of inducing specific antibodies of the IgG class towards the corresponding native extracts, and they have been shown to be remarkably less reactive than said native extracts, as will be evident in the disclosure to follow.

Accordingly, a specific object of the present invention consists in chemically modified allergens having a reduced allergenic activity with respect to the corresponding native allergenic material, and the capability of inducing specific antibodies having an affinity for said native allergenic material, said allergens being characterized in that more than 50% of the primary amino groups of the protein molecule of the native allergen are modified chemically to assume the following structure:

wherein X represents O, S or $NR_2$, wherein $R_2$ is H, an alkyl group having 1-6 carbon atoms, a phenyl group or a CN group, and $R_1$ represents H, an alkyl group having 1-8 carbon atoms, a phenyl group or an arylalkyl group having up to 8 carbon atoms, or an alkyl group containing a heterocyclic ring, said allergens being also characterized in that they are unpolymerized, as well in that they are soluble in a water medium and are resistant to the tryptic attack.

The average percentage of modified primary amino groups should be between 75% and 100% and preferably it should be about 90%. Indeed, it has been found on one side that at substitution degrees lower than 75%, the reactivity of the chemically modified allergenic material is too high and, on the other side, it is possible to arrive at the total substitution only if the chemical treatment is carried out under severe conditions.

It is to be observed that, as the allergenic extracts subjected to chemical modification are made up of heterogeneous protein mixtures, the modification degree is just an average value, so that a value lower than 75% might mean that some allergenic proteins have undergone a poor modification so that they might have kept their allergenic activity at a high degree.

DESCRIPTION OF THE PREFERRED EMBODIMENT

The allergens modified according to the present invention, wherein X=O or S cam be prepared by treatment with an alkaline cyanate (KCNO or NaCNO), or by treatment with organic isocyanates ($R_1$-NCO) or with organic isothiocyanates ($R_1$-NCS) in an alkaline environment. In case of treatment with cyanate, amino groups modified with an unsubstituted carbamyl group are obtained, whereas employing the two other types of reactants, substituted carbamyl derivatives or substituted thiocarbamyl derivatives respectively are obtained. The products of the invention wherein $X=NR_2$ (substituted guanidino derivatives) can be obtained by treatment with compounds of a suitable formula which are capable of giving derivatives.

The reaction occurs at a pH value in the range between 7 and 11, and preferably between 9 and 9.6, while the temperature, in case of treatment with an alkaline cyanate, can be in the range from room temperature and 50° C., preferably between 35° C. and 40° C., the total reaction time being variable between 12 and 36 hours, preferably between 16 and 24 hours.

In case of chemical modification with organic isocyanates or isothiocyanates, both of which are more reactive, it is suitable that the reaction is carried out at room temperature comprised between 0° C. and room temperature or at a temperature, preferably between 0° C. and 5° C., while the total reaction time can vary between 30 minutes and 8 hours, preferably between 2 and 4 hours.

In case of modification performed with reactants suitable to result in a substituted guanidine-type structure, the reaction times, temperature and the possible presence of an organic solvent can all be chosen in the most suitable way by those who are skilled in the art.

The allergenic material to be subjected to the process according to the present invention can be obtained from a substance containing allergens such as pollens, mites, dandruffs, fungi, insect venoms etc. by extracting the substance itself with a suitable solvent, which usually is a water medium, according to well-known procedures. The allergenic extract obtained consists mainly of proteins or glycoproteins, which are usually mixed with impurities like free carbohydrates and pigments, from which the extract is purified for instance by dialysis, precipitation or gel-filtration.

Another extraction procedure that can be employed is that consisting in treating the material containing the allergen or a water extract of the same with a phenol solution, the allergen being then recovered from the phenolic phase. A large description of the techniques available to obtain such aim can be found in J. N. Newell, J. Allergy, 13, 117, 1942.

The resulting allergenic material, after purification performed by any suitable means, can be treated according to the procedure which is the object of the present invention. The chemical modification that is the object of the present finding can equally be carried out on total extracts, on semi-purified or on pure allergens, in mixtures or treated singly.

The chemically modified allergenic material deriving from the same is made up anyway of unpolymerized material.

In case of treatment with cyanate, it is possible for instance to add solid KCNO (freshly recrystallized) to the allergenic extract so that the final concentration is between 0.1 M and 1.5 M, preferably between 0.4 and 0.8 M. The pH of the solution is kept at the desired value by making the allergenic extract 0.1 M in sodium tetraborate by the addition of such salt in the solid state, and possibly making adjustments with 1 M NaOH, if needed.

In case of modification with organic isocyanates or isothiocyanates, as such compounds in some instances are not very soluble in a water medium, it is possible to employ a compatible organic solvent.

When the reaction is over, the chemically modified allergenic extract is subjected to gel-filtration in order to remove the chemical reactant which is present in excess, together with possible degradation products, and so the extract can be put in equilibrium with a suitable salt solution.

The substitution degree obtained can be determined by means of trinitrobenzensulfonic acid titration (as described by Habeeb, Anal. Blochem., 14, 328, 1966) of the amino groups present per mg of the allergenic protein before and after the modification reaction or, more accurately (in case of modification performed by employing an alkaline cyanate) by analyzing the disappearance of lysine from a protein hydrolysed material of the modified allergen, and the appearance of homocitrulline (G. R. Stark and D. G. Smith, J. Biol. Chem. 238, 214, 1963).

The electrophoretic analysis in a polyacrylamide gel in the presence of sodium dodecylsulfate (SDS-PAGE) of a protein endowed with allergenic properties, like ovalbumin, which has undergone a chemical modification which is the object of the present invention, has shown the presence of one only protein band, with molecular weight corresponding to the native protein (45,000 daltons), so showing that the polymerization of the allergen is fully avoided.

The allergenic extract chemically modified according to the procedure disclosed above can be prepared in a water form and administered by parenteral, sublingual, nasal, oral route, or through bronchial route by means of a suitable inhalation device, or as a lyophilized compound to be reconstituted and then administered as appropriate to the water form, or otherwise as a lyophilized compound contained in liposomes or other "drug delivery systems" to be administered through the oral, the parenteral or the inhalation routes or as a powder incorporated in an inert excipient like for instance lactose, to be administered through the nasal or the bronchial routes by means of a suitable inhalation device, or as a powder incorporated in an inert excipient, like for instance lactose and made into tablets which can be possibly also made resistant to gastric secretions through a suitable procedure, for administration through the oral route.

The allergenic extracts modified according to the present invention can be alternatively administered through the parenteral route, once they are adsorbed or co-precipitated by means of compounds like L-tyrosine, aluminum hydroxide or calcium phosphate, or by means of other delayed-release matrixes that favour the slow release of the active principle from the injection site.

The preparations of said modified allergenic extracts can be also realized in the form of an oily suspension, of a syrup, or of an elixir, with the addition of excipients or of compounds that make them palatable for oral administration.

The characteristic monomeric unit nature of the modified allergenic extracts according to the present invention makes them particularly useful, not only for parenteral administration, but also for administration through the nasal, the oral, the sublingual routes or anyway according to all those administration routes that provide a suitable absorption of the active principle through the mucosa to exert their efficiency. Indeed, it is well known that high molecular weight molecules (as for instance the allergenic extracts polymerized with formaldehyde, glutaraldehyde, polyethylene glycols, and so on) are remarkably hindered or they are not capable of crossing the structural anatomical barriers mentioned above.

The therapeutic treatment that provides the oral administration of the modified allergenic extracts according to the method that is the object of the present invention can be particularly effective. Indeed, it is well known that the allergenic proteins which an allergenic extract is made of are remarkably degraded and inactivated by the proteolytic enzymes which are present in the pancreatic secretions; the allergenic extracts modified according to the provisions of the present invention turn out to be on the contrary very resistant to the tryptic treatment, as shown by in vitro experiments. Accordingly, they can show in the optimal conditions to provide a suitable immunogenic stimulus of protective type, probably through Peyer's plaques, an important peripheral lymphoid organ.

According to each one of the administration procedures mentioned above, a specific hyposensitizing therapeutic treatment can be based in a foreseeable way by employing both purified allergens and a mixture of allergens modified according to the procedure which is the object of the present invention, both singly and in a mixture.

The present invention will be disclosed in the following just for examplification but not for limitative purposes in the following preparation examples which are presented together with the experimental tests.

EXAMPLE 1

An aqueous extract (5% weight/volume) from a mixture of pollens of Poa pratensis, Phleum pratense, Holcus lanatus, has been dissolved after lyophilization, with distilled water at about 10 mg of protein/ml (determination according to Lowry). The solution has been then gel-filtered over a Sephadex$^R$ G-25 column (Pharmacia) in order to remove the low molecular weight compounds and to equilibrate simultaneously with a suitable buffer, as for instance 20 mM sodium phosphate buffer at pH 6.86. To the solution so obtained sodium tetraborate decahydrate (3.85 g/100 ml) and with potassium cyanate (4.15 g/100 ml) have been then added. Such salts have been then dissolved by stirring and the pH value has been adjusted to 9.3 by addition of NaOH. The resulting solution has been kept stirred slowly during 20 hours, in a thermostatic bath at 40° C., in a closed flask. The pH of the solution has been kept constant during the first reaction hours by adding 1 M phosphoric acid. When the reaction was over, the resulting solution was gel-filtered again over a Sephadex$^R$ G-25 column in order to remove the cyanate excess employed and it was simultaneously equilibrated with a suitable buffer as for instance the phosphate buffered saline at pH 7.2 (PBS). The preparation so obtained was then filtered in a sterile way on a 0.22 micron membrane (Millipore) and stored within sterilized vials at 4° C. The percentage substitution of the amino groups, determined by the trinitrobenzensulfonic method (TNBS) turned out to be 87%.

In vivo test of the allergenic activity

15 Balb/c mice (5 animals per group), 18–20 g weight were immunized by intraperitoneal administration with 0.25 ml containing 10 mg of an extract of pollen of a Gramineae mixture, as a native extract or as an extract modified with cyanate, in the presence of 1 mg of Al(OH)$_3$. A third group of animals was given just 0.25 ml of PBS+1 mg of Al(OH)$_3$, according to the protocol described for the other groups. 28 days after, each animal was subjected to a booster dose with the same material for the first immunization. After a week, the animals were sacrificed, their bloods were collected according to the group to which they belonged, and then tested for the presence of specific IgEs by mouse-rat passive cutaneous anaphylaxis (Ovary, Int. Archs. Allergy Appl. Immunol., 3, 293, 1952).

The results which are shown in the following Table 1 point out clearly that the capability of inducing specific IgEs of the chemically modified extract of the Gramineae mixture is reduced in a significative way with respect to that shown by the same unmodified extract (p less than 0.01).

TABLE 1

| Mice sensitized with | Mouse-rat passive cutaneous anaphylaxis (PCA) | | | | | | | |
|---|---|---|---|---|---|---|---|---|
| | Dilutions of serum | | | | | | | |
| | 1/2 | 1/4 | 1/8 | 1/16 | 1/32 | 1/64 | 1/128 | 1/256 |
| physiologic solution | − | | | | | | | |
| native extract of pollen of Gramineae mixture | + | + | + | + | + | + | + | |
| modified extract of pollen of Gramineae mixture | + | − | − | − | − | − | − | |

Notes: 100 microl of serial dilutions in a physiological solution of the serum of mice treated with physiological solution+1 mg of Al(OH)$_3$, or with 10 microg of native extract of pollen of a mixture of Gramineae+1 mg of Al(OH)$_3$, or with 10 microg of an extract of a modified pollen of a mixture of Gramineae+1 mg of Al(OH)$_3$, were injected intradermally into Sprague-Dowley rats; after 48 hours these animals were given an intravenous injection of 1 ml of physiological solution containing 1 mg of a native extract of a mixture of Gramineae and 5 mg of Evans Blue. After ½ hr the animals were sacrificed and the presence of characteristic spots was estimated on the skin turned upside down of their backs. The last dilution of the serum that was capable of giving a "spot" of 7 mm size is considered as the PCA titer.

In Vitro Test of the Allergenic Activity (RAST Inhibition)

Polystyrene beads were activated and the native extract of pollen of a mixture of Gramineae was fixed according to a suitable procedure (Western German Patent, DE 3338759C1).

20 microl of the serum of a patient who is allergic to the pollen of Gramineae were pre-incubated at 20° C. in a test-tube for three hours with 30 microl of serial dilutions of the native extract of a mixture of Gramineae or of the same extract modified with cyanate.

Next, a bead sensitized with the extract of a mixture of Gramineae was added to each test-tube, and the whole test-tube was incubated overnight at room temperature; after suitable washings, 50 microl of a solution of $^{125}$I-anti-IgE (Sferikit$^R$, Lofarma Allergeni, Milan, Italy) was added and the whole was incubated for a further time of 16 hours. Each sample was prepared in triplicate.

At the end of the incubation period, the residual radioactivity of the bead was determined by means of a gamma-counter with a counting time of at least one minute. The relative allergenic power is expressed as the amount of the allergenic extract which is capable of inhibiting by 50% the RAST response of a pool of positive sera.

The inhibition rate, from 0 to 100%, was calculated according to L. Yman's formula (Develop. Biol. Standard., 29, 151, 1975):

[(cpm positive control)-(cpm sample)]×100/[(cpm positive control)-(cpm negative control)]

wherein the "negative" and the "positive" control mean respectively the non-specific radioactivity (i.e., the value in cpm obtained by adding the phosphate buffer instead of the patient's serum for the pre-incubation before the addition of the beads sensitized with the respective extract) and the maximum radioactivity (i.e., the value obtained employing the phosphate buffer in substitution for the dilution of the extracts to be tested in inhibition).

The allergenic extract of the Gramineae mixture, modified with cyanate in an alkaline medium has turned out to be significatively less potent than the same unmodified extract (p less than 0.01).

Test of the Immunogenic Activity

New Zealand Black rabbits (Charles River, Calco, Como) were immunized with an emulsion containing 3 mg of native or modified extract of a mixture of Gramineae, in a Freund's adjuvant medium.

Six immunizations were performed, at 21 days from one another; 10 days after the last immunization, a bleeding was carried out and the serum collected from the rabbits which had been treated with the native extract of a mixture of Gramineae or with the modified extract of a mixture of Gramineae was tested separately in an immunodiffusion test (Outcherlony, Progress in Allergy, vol. V, pg. 1–78, Ed. Kallas, P. Karger, New York, 1958) against suitable dilutions of the native extract of a mixture of Gramineae.

Considering as the reference parameter the dilution of the serum which is capable of inducing a precipitation band in the agarose gel, the two samples under test do not show any difference, so confirming the fact that the immunogenic properties (the capability of inducing IgGs cross-reacting with the antigens present in the native extract) of the extract of a mixture of Gramineae modified with cyanate in alkaline medium, are almost unchanged.

Toxicological Analysis

Subchronic toxicity 20 rats of the Sprague-Dowley strain (10 females and 10 males) were treated through the subcutaneous route for 12 weeks with a dose of the cyanate-modified extract of a mixture of Gramineae, which dose was 100 times larger than the clinical proper dose, in order to evaluate any possible toxicological effects.

No pathological fact of relevance was observed even at the histological level in the organs tested (ovaries, spleen, liver, lungs, kidneys, suprarenal glands, heart, thymus, brain, lymphonodes) as a confirmation that chemical modification did not induce any alterations which cause the derived product to show toxicological properties.

Skin Test in Man

Solutions of native extracts of a mixture of Gramineae or of extracts modified with cyanate in an alkaline medium were diluted in a suitable way and then administered intradermally in the volar side of the forearm of patients who are allergic to the pollen of Gramineae.

The results of such experiment can be observed in Table 2 and they refer to the measurement of the diameter of the erythema, performed 15 minutes after the inoculum. The diluting solution was employed as the negative control (Coca+0.03% human albumin).

TABLE 2

| | Skin tests on volunteer patients | | | | | | | | (table follows) |
|---|---|---|---|---|---|---|---|---|---|
| Patient No. | Native extract concentrations (µg/ml) | | | | Modified extract concentrations (µg/ml) | | | | |
| N° | 20 | 4 | 0.8 | 0.16 | 20 | 4 | 0.8 | 0.16 | Diluent |
| 1 | — | — | 50* | 30 | — | — | 18 | 7 | 6 |
| 2 | — | 45 | 34 | 25 | 20 | 11 | 8 | 5 | 5 |
| 3 | 28 | 25 | 18 | 12 | 13 | 8 | 7 | 5 | 6 |
| 4 | 38 | 32 | 32 | 18 | 21 | 9 | 6 | 5 | 5 |
| 5 | — | 37 | 35 | 29 | — | 25 | 19 | 14 | 7 |

*Diameer of the erythema (mm)

As can be observed, the reactivity of the modified extract of a mixture of Gramineae is significatively less than the same unmodified extract (p less than 0.01 at all concentrations considered).

EXAMPLE 2

An aqueous extract (5% weight/volume) from the pollen of Parietaria judaica previously deprived of lipids by ethyl ether was re-hydrated with distilled water after lyophilization, to a concentration of 10 mg/ml (micro-Kjeldhal). After gel-filtration over a Sephadex$^R$ G-25 column, equilibrated with 20 mM phosphate buffer at pH 6.86, the protein solution was subjected to modification through the addition of sodium tetraborate decahydrate (3.85 g/100 ml) and potassium cyanate (4.15 g/100 ml). After possible adjustment of pH value, as shown in example 1, the protein solution in a closed flask was kept under slow stirring for 20 hours in a thermostatic bath. At the end of the reaction, the resulting solution was again gel-filtered over a Sephadex$^R$ G-25 column for separating the purified allergenic extract from the excess modifying reagent. The chromatographic conditions chosen (gel volume/sample volume larger than 5) are suitable to said end: the excess cyanate is eluted quite far from the protein fraction, as can be clearly put into evidence by means of the simple $CoCl_2$ test or by means of other tests reported for instance by W. R. Fearon in Biochem. J., 17, 84, 1923.

The preparation is then filtered in a sterile way on a 0.22 microm membrane (Millipore) and stored in sterilized vials at 4° C. The substitution percentage calculated on the basis of homocitrulline, turned out to be 85%, as the pigments present in the extract of the pollen of Parietaria judaica interferes strongly in the TNBS test.

In Vivo Test of the Allergenic Activity 15 mice of the Balb/c strain (5 animals per each group), 18–20 g weight, were immunized by intraperitoneal administration with 0.25 ml containing 10 microg of native extract of the pollen of Parietaria, or of said extract modified with cyanate in the presence of 1 mg of Al(OH)$_3$. A third group of animals received just 0.25 ml of PBS+1 mg of Al(OH)$_3$, according to the protocol already described for the two other groups.

After 28 days, a booster dose was injected in each animal, employing the same material as that employed for the first immunization.

One week later the animals were sacrificed, their blood samples were collected and pooled according to the group belonged and the respective sere were tested for the presence of specific IgEs by mouse-rat passive cutaneous anaphylaxis.

The results which are shown in the following Table 3 point out clearly that the capability of inducing specific IgEs of the modified extract of Parietaria is significantly reduced with respect to that shown by the unmodified extract of Parietaria (p less than 0.01).

TABLE 3

| Mice sensi-tized with | Mouse-rat passive cutaneous anaphylaxis (PCA) | | | | | Titer* PCA |
|---|---|---|---|---|---|---|
| | Dilutions of sera | | | | | |
| | 1/1 | 1/5 | 1/25 | 1/125 | 1/625 | |
| Diluent | − | | | | | − |
| Native extract of pollen of Parietaria | + | + | + | + | − | 125 |
| Modified extract of pollen of Parietaria | + | − | − | − | − | 1 |

Notes: 100 microl of serial dilutions in a physiological solution of the sera of mice treated with physiological solutions+1 mg of Al(OH)$_3$, or with 10 microg of native extract of pollen of Parietaria or with 10 microg of the modified extract of pollen of Parietaria were injected intradermally into rats of the Sprague-Dowley strain; after 48 hours these animals received an injection through the intravenous route of 1 ml of a physiological solution containing 1 mg of native extract of pollen of Parietaria and 5 mg of Evans Blue. After ½hr the animals were sacrificed and the presence of characteristic spots on the skin turned upside down of the back was estimated. The final dilution of the serum that was capable of giving a so-called "spot" of at least 7 mm was considered as the PCA titer.

In Vitro Test of Allergenic Activity

Polystyrene beads were activated with glutaraldehyde and the native extract of Parietaria judaica fixed according to a suitable procedure (Western Germany patent, DE 3338759C1). 20 microl of the serum of a patient who was allergic to the pollen of Parietaria judaica were pre-incubated at 20° C. in a test-tube for 3 hr with 30 microl of serial dilutions of the native extract of Parietaria or of said extract modified with cyanate in an alkaline medium. Next, a bead sensitized as described in Example 1 was added to each test tube, and the whole sample was incubated overnight at room temperature; after suitable washing, 50 microl of a solution of $^{125}$I anti-IgE was added and the incubation at 20° C. was prolonged for a further period of 16 hr.

The residual radioactivity of the bead for each sample was determined by means of a gamma-counter, with a counting time of at least one minute.

The relative allergenic potency is expressed as the amount of the allergenic extract that is capable of inhibiting by 50% the RAST response of a pool of positive sera.

The inhibition rate, from 0 to 100%, was calculated according to L. Yman's formula (Develop. Biol. Standard. 29, 151, 1975):

[(cpm positive control)-(cpm sample)]×100/[(cpm positive control)-(cpm negative control)]

wherein the "negative" and the "positive" control mean respectively the non-specific radioactivity (obtained by adding the phosphate buffer instead of the patient's serum for the pre-incubation before adding the beads-sensitized with the respective extract), and the maximum radioactivity (obtained employing the RAST buffer in substitution for the dilution of the extracts to be tested for inhibition).

The modified extract of pollen of Parietaria turned out to be significantly less powerful than the same extract when in the native form (p less than 0.01).

Test of Immunogenic Activity

New Zealand Black rabbits (Charles River, Calco, Como) were immunized with emulsion containing 3 mg of extract of pollen of Parietaria, said extract being native or modified with cyanate in a Freund's adjuvant medium.

Six immunizations were performed at intervals of 3 weeks from one another; 10 days after the last immunization, a blood drawing was performed and the serum collected from rabbits treated with the native extract of pollen of Parietaria or with the same extract modified with cyanate was tested separately, by immunodiffusion according to the Outcherlony's procedure against suitable dilutions of the native extract of pollen of Parietaria.

Considering as the reference parameter the dilution of the serum that is capable of inducing a precipitation band in the agerose gel, no significant difference was observed between the two samples under test, so confirming the fact that the immunogenic properties of the extract of pollen of Parietaria modified with cyanate according to the procedure which is the object of the present invention kept almost unchanged.

Toxicological Analysis: Subchronic Toxicity 20 rats of the Sprague-Dowley strain (10 females and 10 males) were treated by the subcutaneous route for 12 weeks with a dose corresponding to 250 microg of extract of pollen of Parietaria modified with cyanate (corresponding to a dose about 100 times larger than the dose set forth for the clinical use).

At the end of the treatment, each animal was sacrificed and its organs were examined for estimating the presence of any possible toxicological damages.

No macroscopic and/or histological pathological remark of relevance was observed in the organs taken into consideration (liver, lungs, spleen, heart, kidneys, suprarenal glands, brain, thymus, ovaries, lymphonodes) so confirming the fact that chemical modification of the extract of pollen from Parietaria did not induce any alterations which cause the derived product to show toxic effects.

Skin Test in Man

The extracts of pollen from Parietaria, in the native form or modified with cyanate according to the example 2 were diluted in a suitable way and then administered intradermally in the volar side of the forearm of patients who were allergic to the pollen of Parietaria.

The results can be observed in Table 4 and they refer to the determination of the diameter of the erythema 15 minutes after inoculum.

The diluting solution (Coca+0.03% human albumin) was employed as the negative control.

TABLE 4

| Patient No. | Skin test | | | | | | |
|---|---|---|---|---|---|---|---|
| | Native extract concentrations (µg/ml) | | | Modified extract concentrations (µg/ml) | | | Diluent |
| | 10 | 0.1 | 0.1 | 10 | 0.1 | 0.1 | |
| 1 | 26* | 21 | 10 | 9 | 6 | 5 | 6 |
| 2 | — | 34 | 26 | — | 12 | 7 | 5 |
| 3 | 28 | 30 | 23 | 20 | 3 | 6 | 7 |
| 4 | 29 | 32 | 25 | 18 | 6 | 7 | 5 |
| 5 | 30 | 21 | 16 | 15 | 7 | 5 | 5 |

*Diameter of the erythema (mm)

As can be deduced from the observation of Table 4, the allergenic reactivity of the extract of pollen of Parietaria modified with cyanate in alkaline medium is significantly reduced (p less than 0.01) with respect to the same extract but not modified.

EXAMPLE 3

An aqueous extract (5% by weight/volume of Dermatophagoides pteronyssinus) (DP) was concentrated by lyophilization, then taken with the minimum volume of a 20 mM sodium phosphate buffer at pH 6.86 and gel-filtered by Sephadex$^R$ G 25, eluting with the same buffer and collecting the excluded peak. 1.92 g of sodium tetraborate decahydrate and 2.05 g of potassium cyanate (freshly recrystallized from 50% ethanol at a temperature not higher than 50° C.) were added to 50 ml of such solution. After dissolving the salts added and after adjusting the pH to 9.3 by means of 1 M NaOH, the gel-filtered extract was kept at 40° C. in a thermostatic bath for 22 hours. In the first hours the pH was adjusted by adding 1 M phosphoric acid. The preparation so obtained was again gel-filtered in order to remove the excess reagent, then sterilized on a 0.22 micron Millipore membrane and stored in aliquots in sterilized vials at 4° C. The substitution percentage of the amino groups, estimated by the TNBS test, turned out to be 84%.

In Vivo Test of Allergenic Activity 15 mice of the Balb/c strain (5 animals per each group), 18–20 g weight, were immunized through intraperitoneal administration with 0.25 ml of a physiological solution containing 10 microg of a native extract of DP or of the same extract modified with cyanate in the presence of 1 mg of Al(OH)$_3$ as the adjuvant. A third group of animals received just 0.25 ml of the physiological solution +1 mg of Al(OH)$_3$ according to the protocol already disclosed above.

After 28 days, each animal was subjected to an immunization boost employing the same material as that employed for the first immunization.

One week after, the animals were sacrificed, their blood samples were gathered into a pool according to the group to which they belonged and the respective sere were tested for the presence of specific IgEs by means of passive cutaneous anaphylaxis.

The results shown in the following Table 5 point out clearly that the capability of the DP extract modified with cyanate in an alkaline medium of inducing specific IgEs is significantly reduced with respect to that shown by the unmodified DP extract (p less than 0.01).

TABLE 5

| | Mouse-rat passive cutaneous anaphylaxis (PCA) | | | | | | | |
|---|---|---|---|---|---|---|---|---|
| | Dilutions of sera | | | | | | | |
| Groups | 1/10 | 1/20 | 1/40 | 1/80 | 1/160 | 1/320 | 1/640 | Titer P.C.A. |
| Diluent | — | — | — | — | — | + | — | — |
| Native DP extract | + | + | + | + | + | + | — | 320 |
| Modified DP extract | + | + | + | — | — | — | — | 40 |

Notes: 100 microl of serial dilutions in a physiological solution of sere of mice treated with physiological solution +1 mg of Al(OH)$_3$ or with 10 microg of native DP extract+1 mg of Al(OH)$_3$ or with modified DP extract+1 mg of Al(OH)$_3$, were injected intradermally into Sprague-Dawley rats; 48 hours after, these animals were given an intravenous injection of 1 ml of physiological solution containing 1 mg of native DP extract and 5 mg of Evans Blue. ½ hr after, the animals were sacrificed and the presence of characteristic spots was estimated on their back skins turned upside down. The last dilution of the serum that was capable of giving a "spot" of 7 mm size was considered to be the PCA titer.

In Vitro Test of Allergenic Activity

Polystyrene beads were activated and the native DP extract was fixed to the same according to a suitable procedure (Western Germany patent DE 3338759C1).

20 microl of the serum of a patient who was allergic to the DP extract was pre-incubated at 20° C. of three hours in test-tubes with 30 microl of serial dilutions of the native DP extract or the same extract modified with cyanate in an alkaline medium.

Next, a bead sensitized with the DP extract (as disclosed above) was added to each test-tube. The whole sample was incubated overnight at room temperature; after suitable washing, 50 microl of human $^{125}$I-antiIgE was added and the whole sample was incubated for a further period of 16 hours.

Each sample was prepared in triplicate. At the end of the incubation period, the residual radioactivity of the bead was determined by means of a gamma-counter employing a counting time of one minute. The relative biological potency of the two extracts examined is expressed as the amount of the extract which is capable of inhibiting by 50% the response of the positive control sample according to the following Yman's formula:

[(cpm positive control)-(cpm sample)]×100/[(cpm positive control)-(cpm negative control)]

wherein "negative" control and "positive" control mean respectively the value of the non-specific radioactivity (obtained by adding the phosphate buffer instead of the patient's serum in the pre-incubation stage before adding the beads bearing the respective extract bonded to them) and the maximum value of radioactivity (obtained employing the buffer in substitution for the extracts to be tested for inhibition).

The allergenic DP extract, modified with cyanate in an alkaline medium turned out to be significantly less powerful than the same unmodified extract, so confirming the reduced allergenic reactivity of the modified extract (p less than 0.01).

EXAMPLE 4

0.05 ml of methyl isocyanate was added to 5 ml of a solution (10 mg/ml) of ovalbumin in a 0.1 M sodium tetraborate buffer at pH 9.3, containing 0.2 M imidazole, which solution was cooled to 0°–4° C. with an ice bath, the addition being carried out with stirring, at the times 0.5', 10'and 15'. After 60 minutes, the protein solution was gel-filtered through a Sephadex$^R$ G-25 column equilibrated with a 20 mM phosphate buffer at pH 6.86 in order to remove the excess methyl isocyanate and its decomposition products.

The substitution degree determined by means of the TNBS test turned out to be 89 %. In the RAST-inhibition test, ovalbumin so modified turned out to be significantly less potent than the unmodified ovalbumin.

EXAMPLE 5

0.05 ml of a 12% (weight/volume) solution of methyl isothiocyanate in acetonitrile was added under stirring and at the times 0', 20', 40', and 80', to 5 ml of a solution (10 mg/ml) of ovalbumin in a 0.1 M sodium tetraborate buffer at pH 9.3, containing a 0.2 M solution of imidazole cooled to 0°–4° C. with an ice bath. After 3 hours, the protein solution was gel-filtered as in the previous example.

The substitution degree determined by means of the TNBS test turned out to be 81%.

In the RAST-inhibition test, the modified ovalbumin turned out to be significantly less potent than the unmodified ovalbumin.

This invention has been disclosed with specific reference to some preferred embodiments of the same, but it is to be understood that modifications and/or changes can be introduced in the same by those who are skilled in the art without departing from the spirit and scope of the invention.

We claim:

1. A chemically modified protein allergen or glycoprotein allergen whose allergenic activity is reduced with respect to that of the corresponding native allergenic material and capable of inducing specific antibodies having an affinity for the corresponding native allergenic material, said allergen is derived from the corresponding native allergenic material by treating the native allergenic material with an organic isocyanate or an organic isothiocyanate is an alkaline medium such that said allergen is unpolymerized, is soluble in a water medium and resists tryptic attack.

2. The allergen according to claim 1, wherein said treatment is carried out with an organic isocyanate or with an organic isothiocyanate at a pH between 7 and 11, at a temperature equal to room temperature or of a temperature comprised between 0° C. and room temperature, and for a total time between 30 minutes and 8 hours.

3. The allergen according to claim 2, wherein the pH during said treatment is between 9 and 9.6.

4. The allergen according to claim 2, wherein the temperature during said treatment is between 0° C. and 5° C.

5. The allergen according to claim 2, wherein the total time of said treatment is between 2 and 4 hours.

* * * * *